US012758972B2

(12) United States Patent
Yamana et al.

(10) Patent No.: US 12,758,972 B2
(45) Date of Patent: Oct. 13, 2026

(54) METHOD AND APPARATUS FOR CONTROLLING FLUID VOLUMES TO ACHIEVE SEPARATION AND PCR AMPLIFICATION

(71) Applicant: Formulatrix International Holding Ltd., Dubai (AE)

(72) Inventors: Kabir Yamana, Bedford, MA (US); Jack Herrera, Bedford, MA (US); Rasmus Lindblom, Bedford, MA (US)

(73) Assignee: Formulatrix International Holding Ltd., Dubai (AE)

( * ) Notice: Subject to any disclaimer, the term of this patent is extended or adjusted under 35 U.S.C. 154(b) by 661 days.

(21) Appl. No.: 18/032,455

(22) PCT Filed: Oct. 19, 2021

(86) PCT No.: PCT/US2021/055638

§ 371 (c)(1),
(2) Date: Apr. 18, 2023

(87) PCT Pub. No.: WO2022/086981

PCT Pub. Date: Apr. 28, 2022

(65) Prior Publication Data

US 2023/0381776 A1 Nov. 30, 2023

Related U.S. Application Data

(60) Provisional application No. 63/093,640, filed on Oct. 19, 2020.

(51) Int. Cl.
*B01L 1/00* (2006.01)
*B01L 3/00* (2006.01)
(Continued)

(52) U.S. Cl.
CPC ... *B01L 3/502715* (2013.01); *B01L 3/502761* (2013.01); *B01L 7/52* (2013.01);
(Continued)

(58) Field of Classification Search
None
See application file for complete search history.

(56) References Cited

U.S. PATENT DOCUMENTS 4,486,152 A 12/1984 Porel
10,625,220 B2 4/2020 Link et al.
(Continued)

FOREIGN PATENT DOCUMENTS

CN 101903104 A 12/2010
CN 104981698 A 10/2015
(Continued)

*Primary Examiner* — Jyoti Mutreja
(74) *Attorney, Agent, or Firm* — E. Eric Mills; Todd A. Serbin; Maynard Nexsen PC

(57) ABSTRACT

An apparatus for controlling fluid volumes, comprising: a motor; a camshaft connected to the motor at a rotational axis of the camshaft; at least one cam disposed on a circumference of the camshaft; a pin frame; at least one pin disposed in the pin frame and operatively associated with the at least one cam, wherein rotation of the camshaft by the motor contacts the at least one cam to the at least one pin, driving the at least one pin in a first direction.

16 Claims, 8 Drawing Sheets

(51) Int. Cl.
*B01L 7/00* (2006.01)
*C12Q 1/6851* (2018.01)
*G01N 21/05* (2006.01)

(52) U.S. Cl.
CPC ........... *C12Q 1/6851* (2013.01); *G01N 21/05* (2013.01); *B01L 2200/027* (2013.01); *B01L 2200/0668* (2013.01); *B01L 2200/10* (2013.01); *B01L 2200/16* (2013.01); *B01L 2300/044* (2013.01); *B01L 2300/0654* (2013.01); *B01L 2300/0672* (2013.01); *B01L 2300/0883* (2013.01); *B01L 2300/0887* (2013.01); *B01L 2300/123* (2013.01); *B01L 2400/0403* (2013.01); *B01L 2400/043* (2013.01); *B01L 2400/0683* (2013.01)

(56) References Cited

U.S. PATENT DOCUMENTS

| | | | |
|---|---|---|---|
| 2003/0129671 | A1 | 7/2003 | Wilding et al. |
| 2006/0094004 | A1 | 5/2006 | Nakajima et al. |
| 2009/0042737 | A1 | 2/2009 | Katz |
| 2010/0304986 | A1 | 12/2010 | Chen et al. |
| 2011/0152681 | A1 | 6/2011 | Reilly |
| 2012/0122108 | A1 | 5/2012 | Handique |
| 2012/0152369 | A1 | 6/2012 | Hiddessen et al. |
| 2012/0244018 | A1 | 9/2012 | Reilly |
| 2013/0252262 | A1 | 9/2013 | Srinivasan et al. |
| 2014/0141498 | A1 | 5/2014 | Enzelberger et al. |
| 2014/0272965 | A1 | 9/2014 | Handique et al. |
| 2015/0136602 | A1 | 5/2015 | Jovanovich et al. |
| 2015/0217293 | A1 | 8/2015 | Faulstich et al. |
| 2016/0296930 | A1 | 10/2016 | Matear et al. |
| 2017/0241949 | A1 | 8/2017 | Bort et al. |
| 2019/0001325 | A1 | 1/2019 | Pais et al. |
| 2019/0256890 | A1 * | 8/2019 | Eberhart .......... G01N 27/44791 |
| 2020/0269239 | A1 | 8/2020 | Johnson et al. |

FOREIGN PATENT DOCUMENTS

| | | | |
|---|---|---|---|
| EP | 2437887 | B1 | 5/2016 |
| EP | 3524973 | A1 | 8/2019 |
| JP | H07/054776 | A | 2/1995 |
| JP | H10196544 | A | 7/1998 |
| JP | 2004309145 | A | 11/2004 |
| JP | 200629798 | A | 2/2006 |
| JP | 2007101428 | A | 4/2007 |
| JP | 200931126 | A | 2/2009 |
| JP | 2009509549 | A | 3/2009 |
| JP | 2011501665 | A | 1/2011 |
| JP | 2012/529268 | A | 11/2012 |
| JP | 2014163773 | A | 9/2014 |
| JP | 2016516195 | A | 6/2016 |
| JP | 2017067595 | A | 4/2017 |
| JP | 201783205 | A | 5/2017 |
| JP | 2017/522545 | A | 8/2017 |
| JP | 2020073912 | A | 5/2020 |
| JP | 2020517916 | A | 6/2020 |
| WO | 2018022971 | A1 | 2/2018 |
| WO | 2019045807 | A1 | 3/2019 |

* cited by examiner

METHOD AND APPARATUS FOR CONTROLLING FLUID VOLUMES TO ACHIEVE SEPARATION AND PCR AMPLIFICATION

CROSS REFERENCE TO RELATED APPLICATIONS

This application is a 35 U.S.C. § 371 U.S. national phase entry of International Application No. PCT/US2021/055638 having an international filing date of Oct. 19, 2021, which claims the benefit of priority under Article 8 PCT of U.S. Provisional Patent Application No. 63/093,640 filed Oct. 19, 2020 and entitled "Point of Collection qPCR System." This application is also related to PCT applications entitled "Fluidic Detection and Control Algorithm for PCR Analysis," "Disposable Cartridge for Reagent Storage and Methods Using Same," and "Apparatuses with Fluidic Channel Geometries for Sample to Answer PCR Analysis and Methods of Using Same," and a U.S. Design application Ser. No. 29/812,034 entitled "Fluidic Channel Geometries of a Chip," all filed concurrently on Oct. 19, 2021 and listing the same Applicant, Formulatrix, Inc. The contents of the above application are all incorporated by reference as if fully set forth herein in their entireties.

FIELD

The present invention, in some embodiments thereof, relates to fluid flow and, more particularly, but not exclusively, to apparatuses and methods for quick and efficient movement of small volumes of fluids.

BACKGROUND

Most current approaches to moving liquids on the microliter scale involve mechanically complicated approaches. Consider a syringe, with a piston sealed against a cylinder. In most systems, this is a direct way to apply pressure or vacuum, however, given the sealing force (O-ring or sealing interface sliding against the cylinder) driving the piston up and down is usually accomplished by a motor rotating a lead screw to drive the relative motion of the piston to the cylinder.

A peristaltic pump is another simpler way, but involves adding or removing discrete volumes of gas or liquid, which can be undesirable in some applications.

Another approach is a centrifugal device, so-called "cd-microfluidics", using different rotational speeds, interfacial features to accomplish liquid motion. See ufluidix.com/circle/whats-a-discman-and-how-is-it-a-medical-diagnostic-device-cd-microfluidics/. While using centrifugal devices may be convenient for some workflows, certain processes, such as real-time quantitative polymerase chain reaction ("qPCR"), cannot currently effectively utilize this mechanism.

SUMMARY

According to an aspect of some embodiments of the present invention, there is provided an apparatus for controlling fluid volumes, comprising: a motor; a camshaft connected to the motor at a rotational axis of the camshaft; at least one cam disposed on a circumference of the camshaft; a pin frame; at least one pin disposed in the pin frame and operatively associated with the at least one cam, wherein rotation of the camshaft by the motor contacts the at least one cam to the at least one pin, driving the at least one pin in a first direction.

In an embodiment of the invention, the camshaft includes a plurality of cams and a plurality of pins, wherein each of the plurality of cams corresponds to one of the plurality of pins.

In an embodiment of the invention, the plurality of cams are disposed on the circumference of the camshaft such that rotation of the camshaft around the rotational axis effectuates driving of the plurality of pins in a desired timing and sequence by utilizing each of the plurality of cams to drive the corresponding pin.

In an embodiment of the invention, the apparatus further comprises a cartridge including a flexible, elastic membrane, wherein the membrane is positioned between the cartridge and the at least one pin.

In an embodiment of the invention, the cartridge includes at least one well formed therein and corresponding to the at least one pin.

In an embodiment of the invention, the at least one pin is spring-loaded by the flexible, elastic membrane.

In an embodiment of the invention, the at least one pin is provided with movement in a second direction, opposite the first direction, by the flexible, elastic membrane.

In an embodiment of the invention, the pin frame comprises at least one slot through which the at least pin passes.

In an embodiment of the invention, the slot of the pin frame positions the at least one pin above a well in a cartridge, the at least one pin located between the cartridge and the at least one cam.

According to a further aspect of some embodiments of the present invention, there is provided system for conducting real-time qPCR analysis, comprising: the apparatus for controlling fluid volumes of claim 1; a cartridge comprising a membrane and at least one well; and, a chip, wherein the at least one well of the cartridge is disposed between the membrane and the chip.

In an embodiment of the invention, the camshaft includes a plurality of cams and a plurality of pins, wherein each of the plurality of cams corresponds to one of the plurality of pins.

In an embodiment of the invention, the plurality of cams are disposed on the circumference of the camshaft such that rotation of the camshaft around the rotational axis effectuates driving of the plurality of pins in a desired timing and sequence by utilizing each of the plurality of cams to drive the corresponding pin.

In an embodiment of the invention, the at least one cam drives the at least one pin into the at least one well.

In an embodiment of the invention, the membrane is elastic.

In an embodiment of the invention, the membrane is disposed between the at least one pin and the at least one well and wherein the membrane forms a fluidic seal with the well when driven by the at least one pin into the well.

In an embodiment of the invention, the at least one pin is provided with movement in a second direction, opposite the first direction, by the flexible, elastic membrane.

According to a further aspect of some embodiments of the present invention, there is provided a method of controlling fluid volumes in a real-time qPCR system, comprising: rotating a camshaft around a rotational axis with a motor; contacting at least one pin with a cam located on the camshaft; driving the at least one pin in a first direction with the cam; depressing a membrane with the at least one pin in a well of a cartridge; and, pushing a fluid within the well using the at least one pin and the membrane.

In an embodiment of the invention, the method further comprises sustaining the rotating to drive at least one additional pin with at least one cam to push an additional fluid within an additional well using the additional pin and the membrane.

In an embodiment of the invention, the rotating effectuates driving of a plurality of pins in a desired timing and sequence to control the flow of fluids out of the cartridge into at least one channel on a chip.

In an embodiment of the invention, the method further comprises moving the at least one pin in a second direction, opposite the first direction, using an elasticity of the membrane.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, are not necessarily to scale and are for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
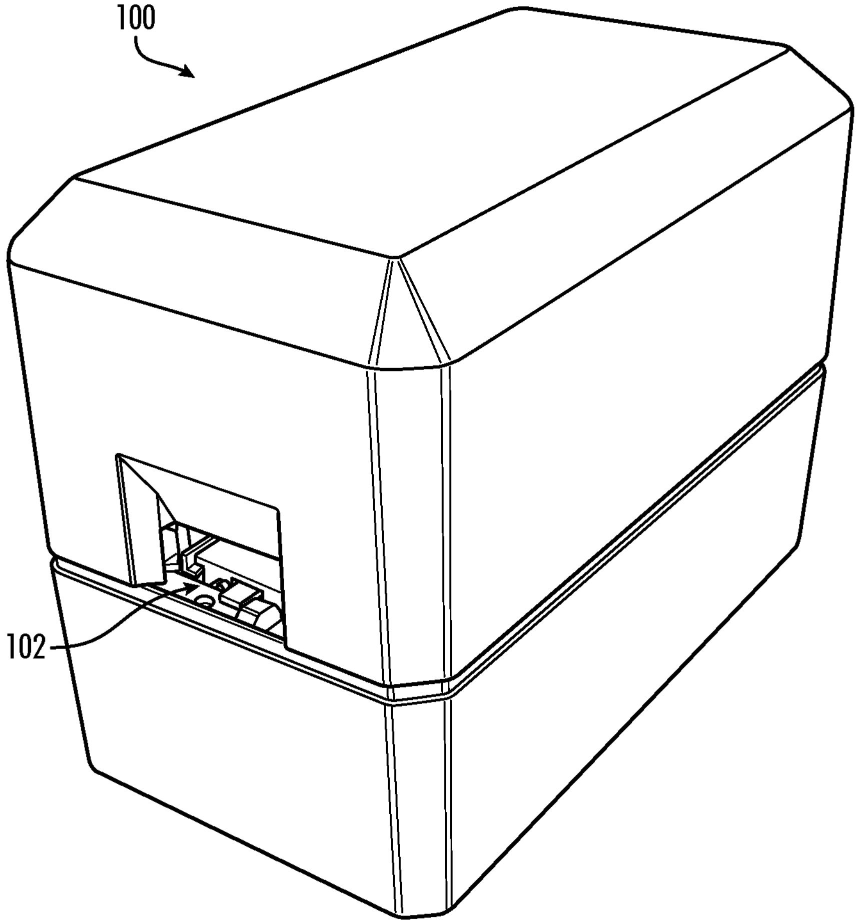
FIG. 1 is a perspective view of a qPCR system, in accordance with an exemplary embodiment of the invention.

The present invention, in some embodiments thereof, relates to fluid flow and, more particularly, but not exclusively, to apparatuses and methods for quick and efficient movement of small volumes of fluids.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Generally, the apparatuses and methods described herein accelerate the process of sample extraction and purification, and subsequent thermal processes of reverse transcription, extension, and denaturing steps of polymerase chain reaction ("PCR") that would occur on the product of the sample purification. The presently described apparatuses and methods quickly and efficiently move small volumes of liquid, optionally a plurality of different liquids located in a plurality of corresponding wells, through one or more and/or a series of channels in a fluid containing cartridge, within a larger system, the larger system used for real time ("RT") qPCR analysis, for example for COVID-19 testing. The solutions described herein use a minimal number of simple parts to effectuate fluid/liquid movement in a desired sequence, very quickly cycling a liquid volume between at least two different regions in a chip of a RT-qPCR system.

Referring now to the drawings, FIG. 1 is a perspective view of a RT-qPCR system 100, in accordance with an exemplary embodiment of the invention. In an embodiment of the invention, and as described in more detail herein and in the related applications filed on same date and referenced in the Related Applications section, a disposable cartridge 406 (shown in more detail with respect to FIGS. 4-8) is inserted into a slot 102 of the RT-qPCR system 100 for analysis. This RT-qPCR system 100 is intended to be quick, conveniently small, easy to use, accurate, affordable and scalable. An exemplary RT-qPCR system 100 will be available from Formulatrix, Inc. of Bedford, MA.

Figure 2:
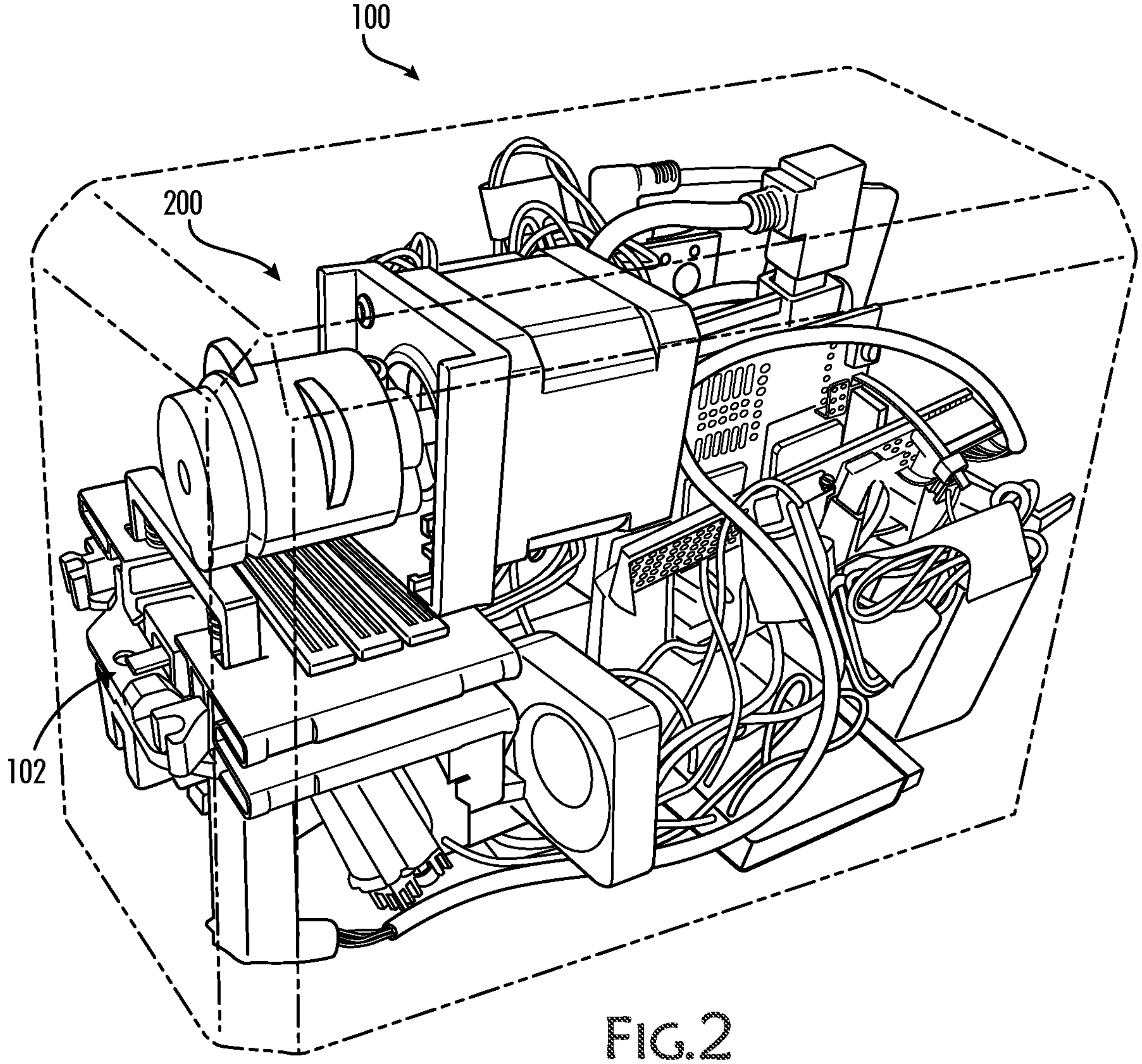
FIG. 2 is a perspective view of a qPCR system with the cover removed, in accordance with an exemplary embodiment of the invention.

FIG. 2 is a perspective view of a RT-qPCR system 100 with the cover removed, in accordance with an exemplary embodiment of the invention. An apparatus for controlling fluid volumes 200 is shown, forming a component part of the RT-qPCR system 100, and shown and described in more detail with respect to FIGS. 3-6.

Figure 3:
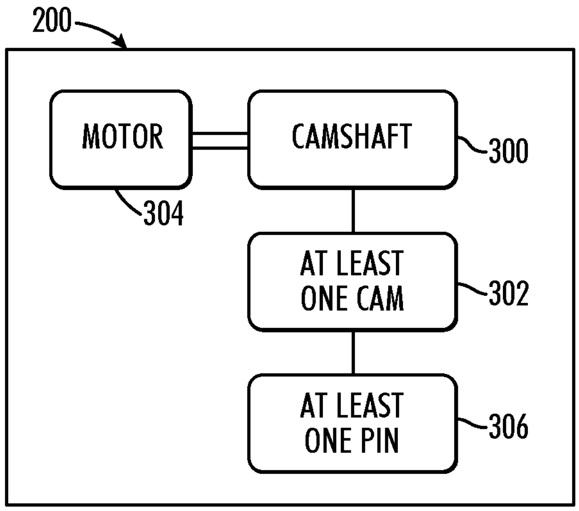
FIG. 3 is a block diagram of an apparatus for controlling fluid volumes, in accordance with an exemplary embodiment of the invention.

FIG. 3 is a block diagram 300 of an apparatus for controlling fluid volumes 200, in accordance with an exemplary embodiment of the invention. In an embodiment of the invention, the apparatus 200 comprises at least one camshaft 300, including at least one cam 302 located on the circumference of the camshaft 300, a motor 304 for driving the camshaft 300, and one or more pins 306 which are driven by the at least one cam 302 of the camshaft 300. It should be understood that the apparatus 200, which itself is a system comprised of multiple parts, is a component part of a larger qPCR system 100. Within this larger RT-qPCR system 100, the apparatus for controlling fluid volumes 200 operatively interacts with the cartridge 406, such as described hereinbelow, in order to effectuate specifically controlled fluidic flow within the cartridge and the overall RT-qPCR system 100.

Figure 4:
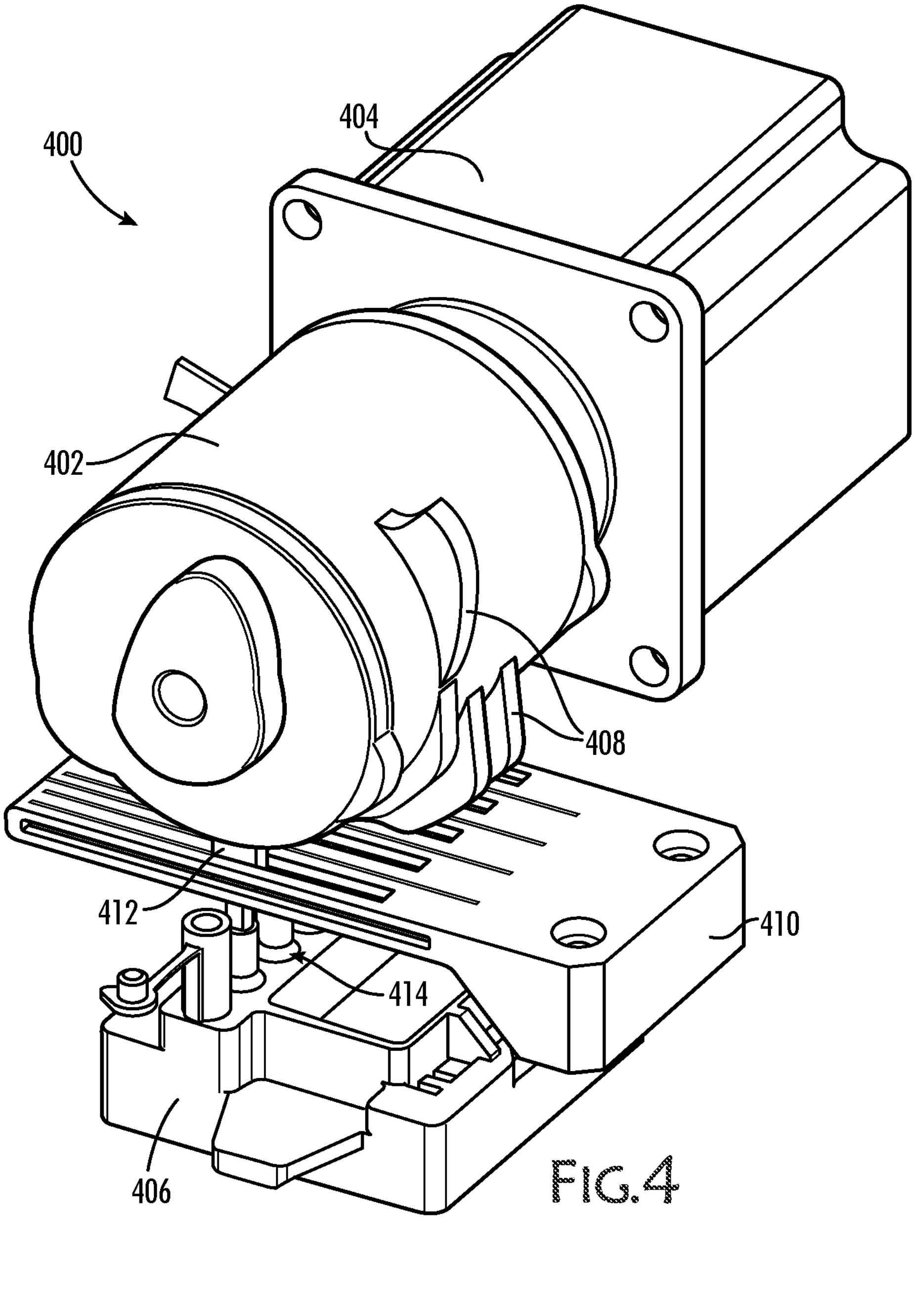
FIG. 4 is a perspective view of an apparatus for controlling fluid volumes, in accordance with an exemplary embodiment of the invention.

FIG. 4 is a perspective view of the apparatus for controlling fluid volumes 400, which is an example of an apparatus for controlling fluid volumes 200, in accordance with an exemplary embodiment of the invention. In the interests of brevity, the apparatus 400 of FIG. 4 is described in conjunction with FIG. 7, a flowchart 700 of a method of using an apparatus 200/400 for controlling fluid volumes. It should be understood that a feature of the present invention is the ability to control a variety of different liquids contained in different fluidic reservoirs/wells in a multi-channel system using only a single rotational axis of the apparatus 200/400, such as described in more detail below. This enables a full sample-to-answer sequence of sample processing to occur with minimal mechanical complexity for actuating or driving the fluids in the system using a membrane positioned above all the working fluids of the system.

In an embodiment of the invention, a camshaft 402 is provided which includes one or more cams 408, wherein the camshaft 402 is rotated (702) in a major rotational axis of the apparatus 400 by a motor 404. In an embodiment of the invention, the motor 404 is a stepper motor. The camshaft 402, and at least one of the cams 408, are operatively positioned such that as the camshaft 402 is rotated is by the motor 404, the at least one cam 408 contacts (704) at least one pin 412, driving (706) the at least one pin 412 into a well 414 of an underlying cartridge 406. In an embodiment of the invention, the at least one pin 412 is operatively positioned in a desired position with respect to its respective cam 408 by a slot of a pin frame 410, where the slot cradles the pin 412 within and therethrough. During the driving (706) a flexible and/or elastic membrane 500 (shown and described in more detail with respect to FIG. 5) is depressed (708) into the well 414 creating a fluidic seal between the membrane 500 and walls of the well 414, and thereby pushing (710) via pressure (e.g. pneumatic pressure) the fluid within the well 414 into the and through a chip 900 positioned under the cartridge 406 (see, for example, the channels 902 of the chip 900 in FIG. 9).

It should be understood that as the camshaft 402 rotates, and the at least one cam 408 is rotated to contact/drive at least one corresponding pin 412, different wells 414 of the cartridge 406 are “activated” by the pushing (710) of the at least one pin 412/membrane 500. In some embodiments of the invention, there are a plurality of pins 412 in the system 400 corresponding to a plurality of wells 414 in the cartridge 406 and rotation of the camshaft 402 around the rotational axis in conjunction with the intentional configuration of the cams 408 on the camshaft effectuate the activation of the pins in a desired timing and/or sequence, allowing for precise introduction of a plurality of fluids located in the wells 414 into the channels 902 of the chip 900 for rapid and automated qPCR analysis.

In some embodiments of the invention, the at least one pin 412 is spring-loaded, or biased, such that when the pin 412 is not being driven (706), it returns to an at-rest, pre-driven configuration. Optionally, the elasticity/resilience of the membrane 500 provides this spring-like behavior to the at least one pin 412. In some embodiments of the invention, the rotating (702) through pushing (710) is repeated (712), for example using additional cams 408 by maintaining rotation of the camshaft 400, to push additional fluids in additional wells, until all of the fluidic wells 414 have been activated, as desired.

In an embodiment of the invention, using the apparatuses and methods described herein, at least one liquid volume is driven across a multitude of different types of regions (within the chip 900), for example, at least one region that is heated to a desired temperature to accomplish PCR amplification and/or at least one region that is subjected to magnetic forces (e.g. for capturing a sample being tested). Additionally, alternatively and/or optionally, at least one portion of a wash fluid is driven past the magnetically captured sample and/or an elution buffer is driven past the at least one magnetized region to elute the magnetically captured sample from the chip 900, or from a component of the chip.

Figure 5:
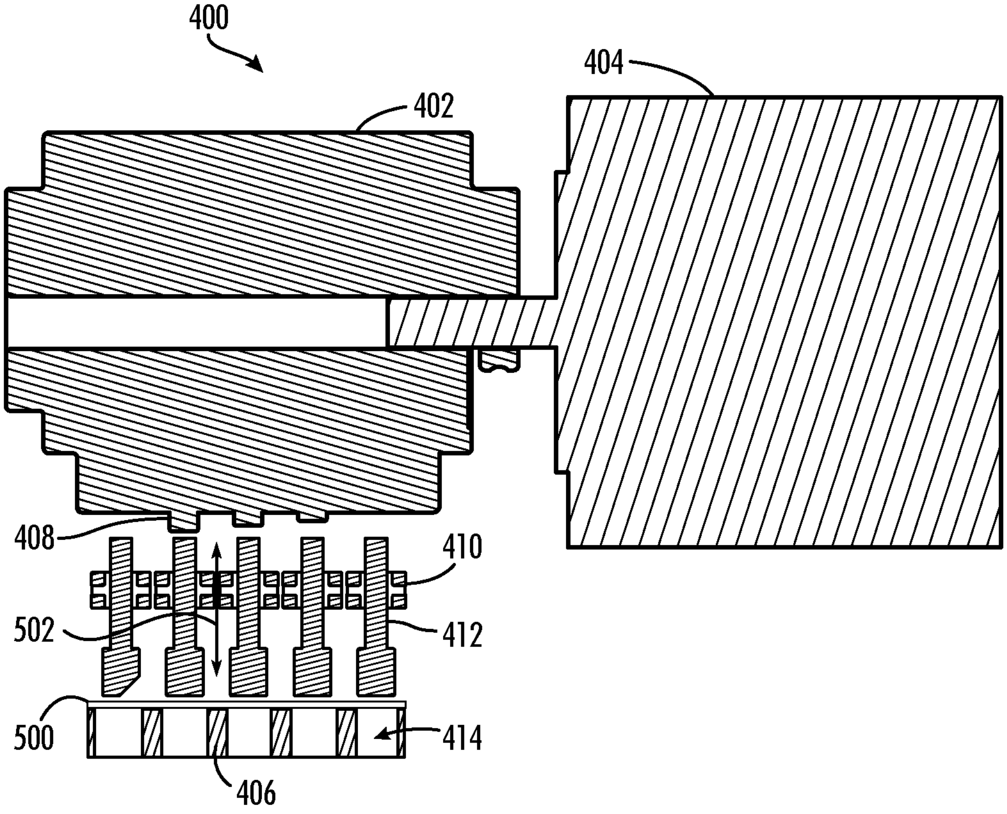
FIG. 5 is a cross-section in a major axis of an apparatus for controlling fluid volumes, in accordance with an exemplary embodiment of the invention.

FIG. 5 is a cross-section in a major axis of the apparatus for controlling fluid volumes 400, in accordance with an exemplary embodiment of the invention. Shown in FIG. 5 is the motion 502 of a pin 412 as a cam 408 drives (706) the pin 412 in a first direction, for example, downwardly (from the perspective of this FIG.) into the membrane 500, thusly, depressing the membrane 500 into the well 414, and then the pin 412 moves in a second direction, for example upwardly, optionally due to the elasticity of the membrane 500 and/or due to being spring-loaded. As described elsewhere herein, insertion of the membrane 500 into the well causes pressure within the well 414 to rise, whereas movement of the membrane 500 out of the well 414 causes the pressure within the well to fall.

Figure 6:
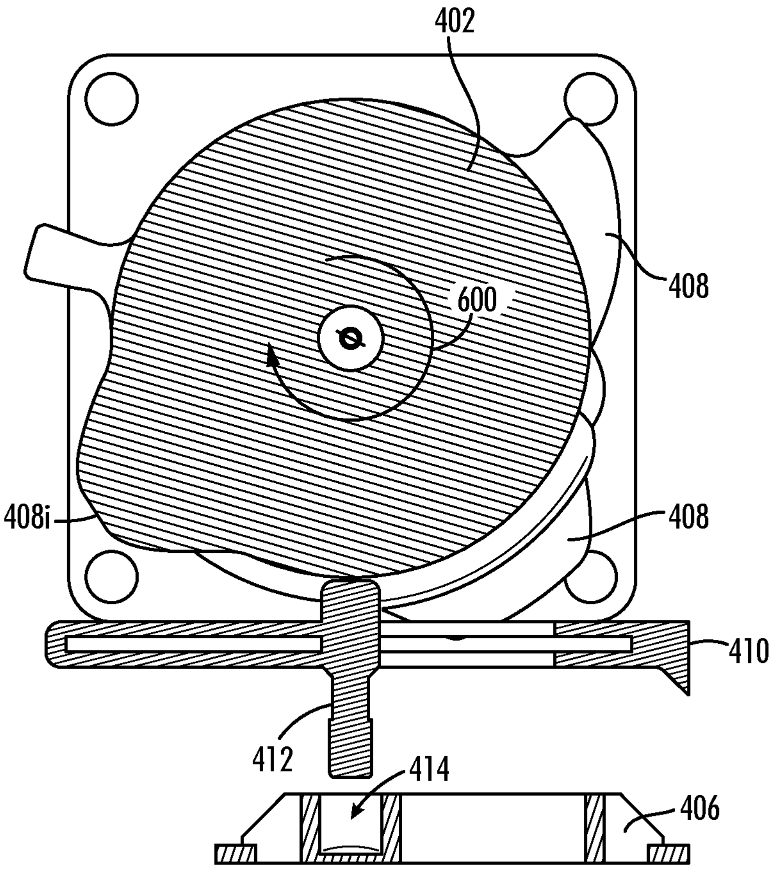
FIG. 6 is a cross-section in a minor axis of an apparatus for controlling fluid volumes, in accordance with an exemplary embodiment of the invention.
Figure 7:
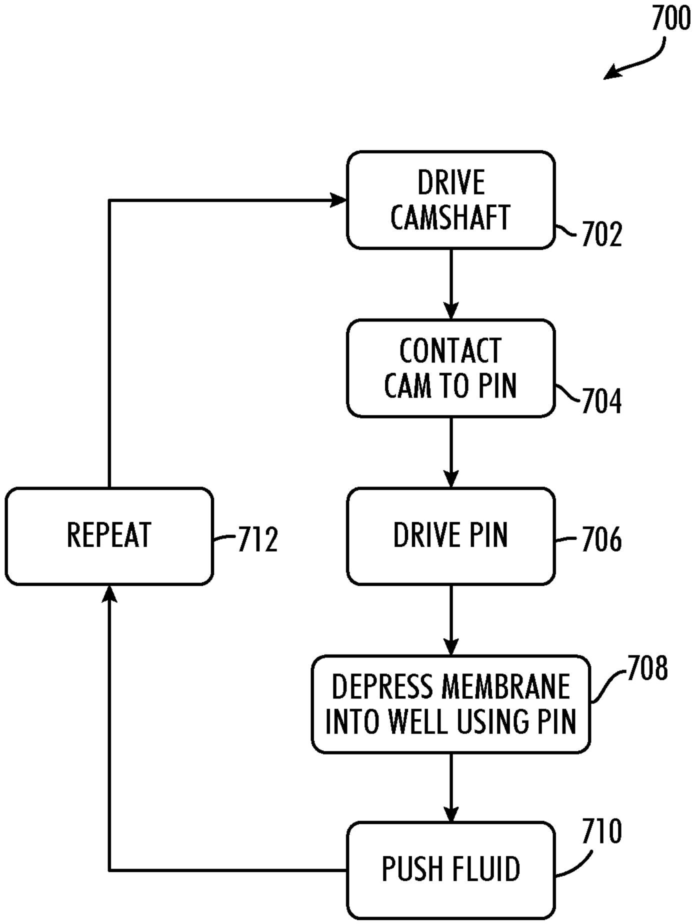
FIG. 7 is a flowchart of a method of using an apparatus for controlling fluid volumes, in accordance with an exemplary embodiment of the invention.

FIG. 6 is a cross-section in a minor axis of the apparatus for controlling fluid volumes 400, in accordance with an exemplary embodiment of the invention. Rotation 600 of the camshaft 402 is shown, wherein the cams 408 are biased for movement in the direction of rotation 600, in an embodiment of the invention. When cam 408*i* rotates around to pin 412, it will drive the pin 412 downwards, through the membrane (not shown) and into the well 414 of the cartridge 406.

Figure 8:
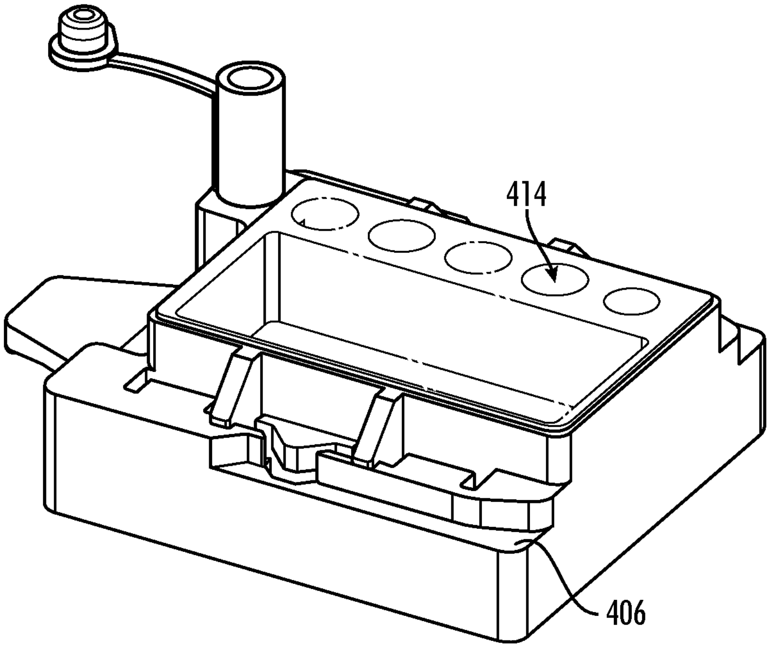
FIG. 8 is a top perspective view of a cartridge, in accordance with an exemplary embodiment of the invention; and, FIG. 9 is a bottom perspective view of a chip, in accordance with an exemplary embodiment of the invention.
Figure 9:
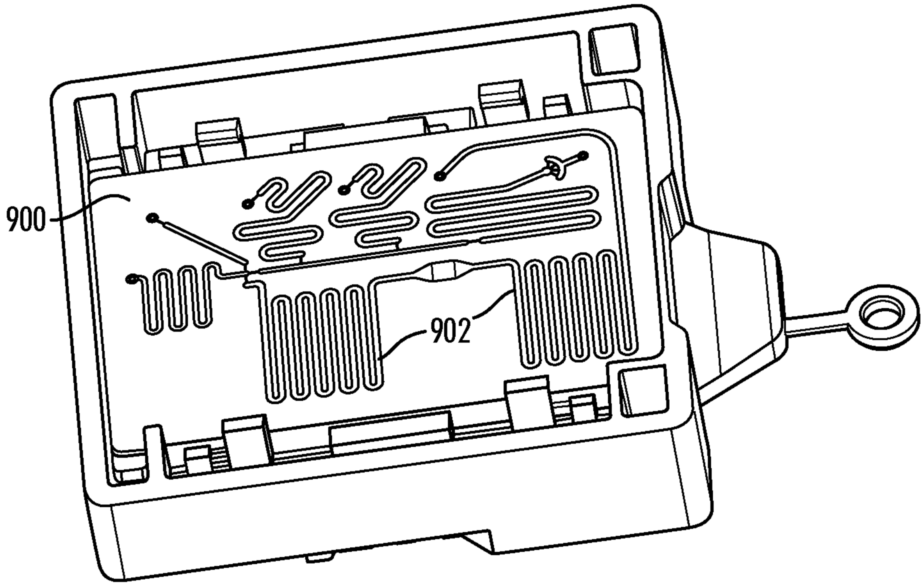

FIG. 8 is a top perspective view of the cartridge 406, in accordance with an exemplary embodiment of the invention. FIG. 9 is a bottom perspective view of the chip 900 seated within the cartridge 406, showing an exemplary configuration of the channels 902, in accordance with an exemplary embodiment of the invention.

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

The term "plurality" means "two or more".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for controlling fluid volumes, comprising:
- a motor;
- a camshaft connected to the motor at a rotational axis of the camshaft;
- at least one cam disposed on a circumference of the camshaft;
- a pin frame;
- at least one pin disposed in the pin frame and operatively associated with the at least one cam; and,
- a cartridge including a flexible, elastic membrane, wherein the membrane is positioned between the cartridge and the at least one pin,
- wherein rotation of the camshaft by the motor contacts the at least one cam to the at least one pin, driving the at least one pin in a first direction,
- wherein the at least one pin is spring-loaded by the flexible, elastic membrane, and
- wherein the at least one pin is provided with movement in a second direction, opposite the first direction, by the flexible, elastic membrane.

2. The apparatus according to claim 1, wherein the camshaft includes a plurality of cams and a plurality of pins, wherein each of the plurality of cams corresponds to one of the plurality of pins.

3. The apparatus according to claim 2, wherein the plurality of cams are disposed on the circumference of the camshaft such that rotation of the camshaft around the rotational axis effectuates driving of the plurality of pins in a desired timing and sequence by utilizing each of the plurality of cams to drive the corresponding pin.

4. The apparatus according to claim 1, wherein the cartridge includes at least one well formed therein and corresponding to the at least one pin.

5. The apparatus according to claim 1, wherein the pin frame comprises at least one slot through which the at least pin passes.

6. The apparatus according to claim 5, wherein the slot of the pin frame positions the at least one pin above a well in a cartridge, the at least one pin located between the cartridge and the at least one cam.

7. A system for conducting real-time qPCR analysis, comprising:
- the apparatus for controlling fluid volumes of claim 1;
- a cartridge comprising a membrane and at least one well; and,
- a chip, wherein the at least one well of the cartridge is disposed between the membrane and the chip.

8. The system according to claim 7, wherein the camshaft includes a plurality of cams and a plurality of pins, wherein each of the plurality of cams corresponds to one of the plurality of pins.

9. The system according to claim 8, wherein the plurality of cams are disposed on the circumference of the camshaft such that rotation of the camshaft around the rotational axis effectuates driving of the plurality of pins in a desired timing and sequence by utilizing each of the plurality of cams to drive the corresponding pin.

10. The system according to claim 8, wherein the at least one cam drives the at least one pin into the at least one well.

11. The system according to claim 8, wherein the membrane is elastic.

12. The system according to claim 11, wherein the membrane is disposed between the at least one pin and the at least one well and wherein the membrane forms a fluidic seal with the well when driven by the at least one pin into the well.

13. The system according to claim 11, wherein the at least one pin is provided with movement in a second direction, opposite the first direction, by the flexible, elastic membrane.

14. A method of controlling fluid volumes in a real-time qPCR system, comprising:

rotating a camshaft around a rotational axis with a motor, contacting at least one pin with a cam located on the camshaft;

driving the at least one pin in a first direction with the cam;

depressing a membrane with the at least one pin in a well of a cartridge; and, pushing a fluid within the well using the at least one pin and the membrane; and, moving the at least one pin in a second direction, opposite the first direction, using an elasticity of the membrane.

15. The method according to claim 14, further comprising sustaining the rotating to drive at least one additional pin with at least one cam to push an additional fluid within an additional well using the additional pin and the membrane.

16. The method according to claim 15, wherein the rotating effectuates driving of a plurality of pins in a desired timing and sequence to control the flow of fluids out of the cartridge into at least one channel on a chip.

* * * * *